United States Patent [19]
Hodson

[11] 3,987,158
[45] Oct. 19, 1976

[54] SEROTONIN ANTAGONISTS

[75] Inventor: Harold Francis Hodson, London, England

[73] Assignee: Burroughs Wellcome Co., Research Triangle Park, N.C.

[22] Filed: Jan. 29, 1974

[21] Appl. No.: 437,738

Related U.S. Application Data

[63] Continuation of Ser. No. 708,532, Feb. 27, 1968, abandoned, which is a continuation-in-part of Ser. Nos. 469,892, July 6, 1965, abandoned, and Ser. No. 602,139, Dec. 16, 1966, abandoned.

[30] Foreign Application Priority Data

Dec. 23, 1965 United Kingdom............... 54489/65
July 7, 1964 United Kingdom............... 27989/64
Oct. 29, 1974 United Kingdom............... 44171/74

[52] U.S. Cl................................. 424/9; 424/275; 424/326; 260/564 R
[51] Int. Cl.$^2$................. A61K 29/00; A61K 31/38; A61K 31/155
[58] Field of Search...................... 424/275, 326, 9; 260/564

[56] References Cited
UNITED STATES PATENTS

| | | | |
|---|---|---|---|
| 2,450,386 | 9/1948 | Short et al. ........................ | 260/564 |
| 2,451,779 | 10/1948 | Short et al. ........................ | 260/501 |
| 3,105,853 | 10/1963 | McKay et al. ..................... | 260/564 |
| 3,179,668 | 4/1965 | Schickh et al. ................... | 260/309.6 |

Primary Examiner—Sam Rosen
Attorney, Agent, or Firm—Donald Brown

[57] ABSTRACT

A compound of the formula

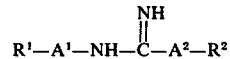

or an acid addition salt thereof wherein $R^1$ and $R^2$ are the same or different and each is a phenyl or thien-2-yl group optionally substituted in one or more positions by a substituent selected from the class consisting of halogen, lower alkyl, lower alkoxy, hydroxy, lower alkylthio, phenyl, phenoxy, phenyl-(lower-alkyl) and phenyl-(lower-alkoxy), each of the said phenyl, phenoxy, phenyl-(lower-alkyl) and phenyl-(lower-alkoxy) substituent groups being optionally substituted in one or more positions by a member selected from the class consisting of halogen, lower alkyl, lower alkoxy, hydroxy, and lower alkylthio;

$A^1$ is a divalent straight or branched alkylene group containing from two to six carbon atoms and one or two divalent atoms which are each an oxygen or sulphur atom, provided that there are at least two carbon atoms between the divalent atom and the —NH— group and between the two divalent atoms; and $A^2$ is the methylene group —$CH_2$—.

35 Claims, No Drawings

SEROTONIN ANTAGONISTS

This is a continuation of application Ser. No. 708,532, filed Feb. 27, 1968, which is a continuation-in-part of application Ser. No. 469,892 filed July 6, 1965, and Ser. No. 602,139, filed Dec. 16, 1966, respectively, all now abandoned.

The present invention relates to chemical compounds, to the method of preparing them and to pharmaceutical compositions containing them, and especially to novel chemical compounds having, in particular, a valuable pharmacological activity.

5-Hydroxytryptamine is a substance whose biochemical and physiological significance is gradually being elucidated. It is present in the brain. It is produced in relatively large amounts in carcinoid tumours. It may also be of importance in allergic conditions such as asthma, dermatitis and hay fever, in certain types of hypertension, in acute gout and in migraine. Moreover, it may be of importance in thrombus formation.

It is an object of the present invention to provide valuable novel chemical compounds.

Moreover, it is an object to provide novel chemical compounds which are valuable specific antagonists of 5-hydroxytryptamine.

Furthermore, it is an object to provide novel chemical compounds which may be used for antagonising the physiological effects of 5-hydroxytryptamine.

Specifically, and in particularly preferred features, it is an object of the present invention to provide novel chemical compounds which, by virtue of their antagonism of 5-hydroxytryptamine, may be useful in treating migraine, controlling thrombus formation, treating inflammatory states and allergic conditions, assisting in hypertensive states, in general in central nervous system therapy, and/or in the relief of acute gout.

A further object of the present invention is to provide compounds of value in laboratory and clinical studies of the in vitro and in vivo pharmacological effects of 5-hydroxytryptamine, and of value in studying the physiological and pathological mechanisms which are believed to involve the formation of 5-hydroxytryptamine.

These various objects are, however, in no way limiting on the scope of the present invention, and indeed further objects will appear from the following description.

The present invention is based on the discovery that the compounds of the formula (I) below and the acid addition salts thereof, which are novel compounds, are specific antagonists of 5-hydroxytryptamine, in that they antagonise the pressor effect of intravenous 5-hydroxytryptamine in pithed rats, the contracting effect of 5-hydroxytryptamine on isolated rat uterus, and the inflammatory effect of 5-hydroxytryptamine when it has been injected into the plantar surface of rat feet.

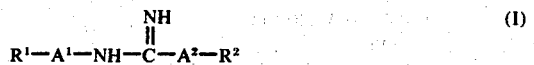

(I)

$R^1$ and $R^2$ are the same or different and each is a phenyl or thien-2-yl group optionally substituted in one or more positions by a substituent selected from the class consisting of halogen, lower alkyl, lower alkoxy, hydroxy, lower alkylthio, phenyl, phenoxy, phenyl-(loweralkyl) and phenyl-(loweralkoxy), each of the said phenyl, phenoxy, phenyl-(lower-alkyl) and phenyl-(lower-alkoxy) substituent groups being optionally substituted in one or more positions by a member selected from the class consisting of halogen, lower alkyl, lower alkoxy, hydroxy, and lower alkylthio;

$A^1$ is a divalent straight or branched alkylene group containing from two to six carbon atoms and one or two divalent atoms which are each an oxygen or sulphur atom, provided that there are at least two carbon atoms between the divalent atom and the —NH— group and between the two divalent atoms; and $A^2$ is the methylene group —$CH_2$—.

In the above definitions of $R^1$ and $R^2$, the term "lower" as applied to 'alkyl' or 'alkoxy' groups or the 'alkyl' or 'alkoxy' moieties of a group, means an 'alkyl' or 'alkoxy' group having 1 to 4 carbon atoms.

The activity of the compounds of formula (I) and the acid addition salts thereof resides in the bases. Therefore, the acid in the acid addition salts is of minor importance though it is preferably pharmacologically and pharmaceutically acceptable. For example, the acid is hydrochloric, sulphuric, p-toluenesulphonic, p-chlorobenzenesulphonic, maleic or tartaric acid.

The present invention in one aspect provides the compounds of formula (I) and the acid addition salts thereof.

Among the preferred compounds of formula (I) are those wherein $R^1$ is substituted by phenyl, benzyl, phenoxy, and phenoxy(lower-alkoxy), the group $R^2$ being optionally substituted by other substituents referred to above. Alternatively, the group $R^1$ in the compounds of formula (I) is a phenyl ring, optionally substituted at the 3-position with a halogen atom or a lower alkyl or lower alkoxy group, or $R^1$ is an unsubstituted thien-2-yl group. Desirably the substituent in the phenyl ring is a chlorine or bromine atom or an alkyl or alkoxy group having 1, 2 or 3 carbon atoms, and so far it has been found that generally the compounds of this invention exhibit the highest activity when the substituent is a chloro, methoxy or ethyl group or, though to a slightly lower extent, an ethoxy or methyl group.

The group $A^1$ in the compounds of the invention has been found to be most advantageously the oxyalkylene group —$O.R^3$—, when $R^1$ is phenyl or substituted phenyl as hereinbefore defined, $R^3$ being a divalent straight or branched alkylene group containing from 2 to 4 carbon atoms. When the group $A^1$ is an oxyalkylene group containing more than 4 carbon atoms, or when the group is a thioalkylene group, the activity of the compounds is significant but tends to be usually of a somewhat lower order. When the group $R^1$ is a thien-2-yl group, the group $A^1$ is advantageously the methyleneoxyalkylene group —$CH_2OR^3$—, the group $R^3$ being as defined hereinbefore; compounds of this type also exhibit an especially high activity. Furthermore, in detail, the activity of the compounds seems to depend on the alkylene group —$R^3$—, and generally in order of gradually decreasing activity, the preferred alkylene groups are the butyl-2,3-ene(—$CH(CH_3).CH(CH_3)$—), isopropylene and ethylene (—$(CH_2)_2$—) groups, the 2-propyl-1-ene (—$CH(CH_3).CH_2$—) and the 1-propyl-2-ene (—$CH_2.CH(CH_3)$—) groups being substantially equivalent.

The group $R^2$ is desirably a phenyl group, and advantageously this is substituted at the 3-position, the 4-position, the 2,4-positions, the 3,5-positions or the 3,4-positions, the substituent(s) being preferably a halogen atom or a lower alkyl or lower alkoxy group. Generally the more active compounds seem to be those wherein each substituent is a chlorine atom or a methyl or methoxy group. Examples of these are 3-methyl, 4-methyl, 2,4-dichloro, 3-methoxy, 3,5-dimethyl, 2,4-dimethyl, and 3,4-dimethyl. Generally, the most active compounds seem to be those wherein $R^2$ is substituted in the 3-position or 3,4-positions, preferably with methyl or chlorine.

Specifically, within these various generalisations, the following compounds and their acid addition salts have been found so far to be preferred in that they are especially active specific antagonists of 5-hydroxytryptamine:

N-(2-3'-methylphenoxypropyl) phenylacetamidine;
N-(2-2'-thenyloxypropyl)-4-chlorophenylacetamidine;
N-(2-3'-ethoxyphenoxypropyl)phenylacetamidine;
N-(2-3'-methoxyphenoxypropyl)-4-bromophenylacetamidine;
N-(2-3'-chlorophenoxyethyl)-4-chlorophenylacetamidine;
N-(2-3'-ethoxyphenoxypropyl)-4-chlorophenylacetamidine; and
N-(2-3'-methylphenoxyethyl)-3-methylphenylacetamidine.

Furthermore, the following compounds and their acid addition salts are particularly preferred since they exhibit an especially high activity:

N-(2-3'-ethylphenoxypropyl)phenylacetamidine;
N-(2-phenoxypropyl)-4-methylphenylacetamidine;

Moreover, the following compounds and their acid addition salts are especially advantageous in that their specific antagonistic activity is exhibited over a relatively prolonged period:

N-(2-3'-chlorophenoxypropyl)-4-chlorophenylacetamidine; and
N-(2-3'-methylbenzyloxypropyl)-4-chlorophenylacetamidine.

Furthermore, the following compounds and their acid addition salts are particularly preferred in that not only are they especially active specific antagonists of 5-hydroxytryptamine, but also their activity is exhibited over a relatively prolonged period.

N-(2-3'-ethylphenoxypropyl)-4-chlorophenylacetamidine;
N-(2-3'-methoxyphenoxypropyl)-phenylacetamidine;
N-(2-3'-chlorophenoxypropyl)-phenylacetamidine;
N-(2-3'-methoxyphenoxypropyl)-3-chlorophenylacetamidine;
N-(2-3'-methylphenoxypropyl)-4-bromophenylacetamidine;
N-(2-3'-methylphenoxypropyl)-3-chlorophenylacetamidine;
N-(2-3'-propoxyphenoxypropyl)-4-chlorophenylacetamidine;
N-(2-3'-methoxyphenoxypropyl)-3-methoxyphenylacetamidine;
N-(2-3'-methoxyphenoxyethyl)-3-methylphenylacetamidine; and
N-(2-3'-methylphenoxypropyl)-4-methylphenylacetamidine.

Moreover, the following compounds and their acid addition salts are particularly preferred since they exhibit a very high activity coupled with a relatively prolonged period of action:

N-(2-3'-methoxyphenoxypropyl)-4-chlorophenylacetamidine;
N-(1-3'-methylphenoxyprop-2-yl)-4-chlorophenylacetamidine;
N-(2-phenoxybut-3-yl)-4-chlorophenylacetamidine;
N-(2-3'-methylphenoxypropyl-3-methylphenylacetamidine;
N-(1-3'-methoxyphenoxyprop-2-yl)-4-chlorophenylacetamidine;
N-(1-phenoxyprop-2-yl)-3-methylphenylacetamidine;
N-(2-2'-thenyloxypropyl)-3-methylphenylacetamidine;
N-(2-3,5-dimethoxyphenoxypropyl)-3-methylphenylacetamidine;
N-(2-phenoxypropyl)-3,4-dimethylphenylacetamidine;
N-(4-3'-methoxybutyl)-3,4-dimethylphenylacetamidine; and
N-(2-2'-thenyloxypropyl)-3,4-dimethylphenylacetamidine.

Additionally, the following compounds and their acid addition salts are especially preferred because not only are they highly active antagonists of 5-hydroxytryptamine, but also their activity, which is relatively prolonged, appears to be greater five hours after administration than one hour after administration:

N-(2-3'-methylphenoxypropyl)--chlorophenylacetamidine; -chlorophenylacetamido;
N-(2-3'-methylphenoxybut-3-yl)-4-chlorophenylacetamidine;
N-(2-3'-methoxyphenoxypropyl)-3,4-dimethylphenylacetamidine;
N-(2-phenoxypropyl)-3-methylphenylacetamidine;
N-(2-3'-methoxyphenoxypropyl)-3-methylphenylacetamidine;
N-(2-3'-methylphenoxypropyl)-3,4-dimethylphenylacetamidine; and
N-(1-3'-methoxyphenoxyprop-2-yl)-3,4-dimethylphenylacetamidine.

Of this last group of compounds, the last four are preferred at this time above any of the other compounds previously listed.

The following compounds and their acid addition salts have also been found so far to be preferred in that they are especially active specific antagonists of 5-hydroxytryptamine;

N-[2-(5-chloro-2-thenyloxy)ethyl]-m-methylphenylacetamidine;
N-[2-(5-chloro-2-thenyloxy)propyl]-3,4-dimethylphenylacetamidine;
N-(2-m-chlorobenzyloxypropyl)-3-methylphenylacetamidine;
N-[2-(5-chloro-2-thenyloxy)propyl]-m-methylphenylacetamidine;
N-(2-m-chlorobenzyloxypropyl)-3,4-dimethylphenylacetamidine;
N-(2-m-methoxyphenoxypropyl)-3,4-dichlorophenylacetamidine;
N-(2-m-fluorophenoxypropyl)-3,4-dimethylphenylacetamidine;
N-(2-m-chlorophenoxypropyl)-3,4-dimethylphenylacetamidine;
N-(2-m-fluorophenoxypropyl)-m-methylphenylacetamidine;
N-(2-o-chlorobenzyloxypropyl)-3,4-dimethylphenylacetamidine;

N-(2-o-chlorobenzyloxypropyl)-m-methyl-phenylacetamidine;

N-(2-m-bromophenoxypropyl)-m-methyl-phenylacetamidine;

N-(2-m-bromophenoxypropyl)-3,4-dimethyl-phenylacetamidine;

N-[2-m-(methylthio)phenoxypropyl]-3,4-dimethyl-phenylacetamidine;

N-(2-m-methylthiophenoxypropyl)-m-methyl-phenylacetamidine;

N-(2-m-t-butylphenoxypropyl)-3,4-dimethyl-phenylacetamidine;

N-(2-phenylthiopropyl)-m-methylphenylacetamidine;

N-(2-m-methoxyphenylthiopropyl)-3,4-dimethyl-phenylacetamidine;

N-(2-2'-phenoxyethoxyethyl)-3,4-dimethyl-phenylacetamidine;

N-(2-m-phenoxyphenoxypropyl)-3,4-dimethyl-phenylacetamidine;

N-(2-m-benzylphenoxypropyl)-3,4-dimethyl-phenylacetamidine;

N-(2-3'-benzyloxyphenoxypropyl)-3-methyl-phenylacetamidine;

N-(2-2'-benzyloxyphenoxypropyl)-4-chloro-phenylacetamidine;

N-(2-3'-phenylphenoxypropyl)-3,4-dimethyl-phenylacetamidine;

N-(2-3'-phenylphenoxypropyl)-3-methyl-phenylacetamidine;

N-2-3'-benzyloxybenzyloxypropyl)-4-chloro-phenylacetamidine;

N-(2-4'-benzyloxyphenoxypropyl)-3,4-dimethyl-phenylacetamidine;

N-(2-3'-methoxyphenoxypropyl)-3-benzyloxy-phenylacetamidine; and

N-(2-3'-phenoxyphenoxypropyl)-3-methyl-phenylacetamidine.

The compounds of formula (I) and the acid addition salts thereof may be prepared by any convenient or known method for preparing amidines.

Thus, they may be prepared by reacting an imidocarbonyl compound with ammonia, a primary amine or a reducing agent.

The imidocarbonyl compound may be a nitrile, imidoester, imidyl halide, thioamide, amidine or amidoxine.

For example, the compounds of the invention are conveniently prepared by reacting ammonia with an imidocarbonyl compound of the formula:

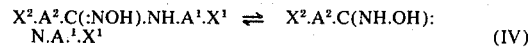

wherein $Y^1$ is a halogen atom or a mercapto, alkylthio or alkoxy group, the alkyl group in the last two having desirably not more than 6 carbon atoms; or by reacting a primary amine $X^1.A^1.NH_2$ with an imidocarbonyl compound of the formula:

wherein $Y^2$ is a hydrogen atom and $Y^3$ an amino, mercapto, alkylthio or alkoxy group, the alkyl group in the last two having desirably not more than 6 carbon atoms, or $Y^2$ and $Y^3$ together form a bond; or by reacting an imidocarbonyl compound of the formula:

$$X^2.A^2.C(:NOH).NH.A^1.X^1 \rightleftharpoons X^2.A^2.C(NH.OH): N.A^1.X^1 \qquad (IV)$$

the two forms being tautomeric, with a reducing agent.

More specifically, the compounds may be prepared by reacting a primary amine with a nitrile according to the equation:

i. $X^2.A^2.CN + H_2N.A^1.X^1 \rightarrow$ (I)

The reaction may be performed in the presence of sodium or sodamide, or of a condensing agent such as aluminium chloride, but is preferably effected using an acid addition salt of the primary amine. The acid is, for example, p-toluenesulphonic or p-chlorobenzenesulphonic acid. Desirably the reaction is performed in the absence of a solvent, conveniently at a temperature above 180° C.

The compounds of formula I and the acid addition salts thereof may also be prepared specifically by reacting an imidoester with a primary amine according to the equation:

ii. $X^2.A^2C(:NH).Z + H_2N.A.^1.X^1 \rightarrow$ (I) + HZ.

wherein Z is an alkylthio or alkoxy group, in which the alkyl group has desirably not more than 6 carbon atoms. The preferred alkylthio group is the methylthio group whilst the preferred alkoxy group is the ethoxy group. Conveniently the imidoester may be in the form of an acid addition salt, advantageously a hydrogen halide such as a chloride, bromide or iodide. The reaction is usually effected in the presence of a solvent, for example, an alkanol such as ethanol.

The compounds of formula I and the acid addition salts thereof may, furthermore, be prepared specifically by reacting a primary amine with a thioamide according to the following equation, the thioamide being shown in one form whilst its tautomeric form is, of course, $X^2.A^2.C(SH):NH$:

iii. $X^2.A^2.CS.NH_2 + H_2N.A^1.X^1 \rightarrow$ (I) + $H_2S$

The reaction is conveniently effected in the presence of a solvent, for example, an alkanol such as ethanol, desirably at an elevated temperature. A heavy metal salt such as a salt of mercury or zinc, for example, a halide, may be included in the reaction mixture.

The compounds of formula I and the acid addition salts thereof may, moreover, be prepared specifically by reacting an amidine with a primary amine according to the equation:

iv. $X^2.A^2.C(:NH).NH_2 + H_2 N.A.^1.X^1 \rightarrow$ (I) + $NH_3$

Conveniently the reaction is effected in the presence of a solvent, for example, benzene or an alkanol such as ethanol, most desirably at an elevated temperature, say, between 30° C and the boiling point of the reaction mixture. The primary amine may be used in the form of an acid addition salt.

Furthermore, the compounds of formula I and the acid addition salts thereof may be prepared specifically by reacting an imidyl halide with ammonia according to the equation:

v. $X^2.A^2.C (:N.A^1.X^1). Ha + NH_3 \rightarrow$ (I) + HHa wherein Ha is a halogen atom. The halide is preferably the chloride, and the reaction may advantageously be effected at an elevated temperature. The imidyl halide starting material is preferably formed by reacting the corresponding amide with a halogenating agent such as phosphorus pentachloride.

Also, the compounds of formula I and the acid addition salts thereof may be prepared specifically by reacting an imidoester with ammonia according to the equation:

vi. $X^2.A^2.C(:N.A^1.X^1).Z + NH_3 \rightarrow (I) + HZ$ wherein Z is as defined hereinbefore. The reaction is preferably performed according to the conditions indicated above for the reaction of equation (ii).

Moreover, the compounds of formula I and the acid addition salts thereof may be prepared specifically by reacting a thioamide with ammonia according to the following equation, the thioamide being shown in one form whilst its tautomeric form is, of course, $X^2.A^2C(.SH):N.A^1.X^1$:

vii. $X^2.A^2.OS.NH.A^1.X^1 + NH_3 \rightarrow (I) + H_2S$

The reaction is advantageously effected under conditions similar to those indicated above for the reaction according to equation (v).

Again, the compounds of formula I and the acid addition salts thereof may be prepared specifically by reacting an amidoxime with a reducing agent according to the equation:

viii. $X^2.A^2.C(:NOH).NH.A^1.X^1 \xrightarrow{reduction} (I)$

The reduction is preferably achieved using hydrogen in the presence of a hydrogenation catalyst, such as Raney nickel.

The product formed by any of the reactions will be an amidine base or an acid addition salt thereof, and these may be converted by double decomposition (metathesis) respectively into salts or into bases or other salts by reaction with an acid or salt thereof or with a base, acid or salt thereof as appropriate. The reaction may be effected in solution or on an ion exchange column. Salts such as hydriodides, hydrochlorides, sulphates, lactates, citrates, tartrates, succinates, oxalates, p-toluenesulphonates, p-chlorobenzenesulphonates and maleates may thus be prepared.

The present invention, in another aspect, provides the above described methods of preparing the compounds of formula I and the acid addition salts thereof.

The compounds of formula I and the acid addition salts thereof may be presented with an acceptable carrier therefor in pharmaceutical compositions. The compositions may be made by any convenient method comprising bringing the components into association with each other, for example, by admixture. For oral administration, fine powders or granules of the compound or salt may contain diluents and dispersing and surface active agents, and may be presented in a draft in water or in syrup; in capsules or cachets in the dry state or in a non-aqueous suspension, when a suspending agent may also be included; in tablets, when binders and lubricants may also be included; or in a suspension in water or a syrup or an oil or in a water/oil emulsion, when flavouring, preserving, suspending, thickening and emulsifying agents may also be included; the granules or the tablets may be coated, and the tablets may be scored. For parenteral administration, the compound or salt may be presented in unit dose or multidose containers in aqueous or non-aqueous injection solutions which may contain anti-oxidants, buffers, bacteriostats and solutes which render the compound or salt isotonic with the blood; or in aqueous or non-aqueous injection suspensions, when suspending agents and thickening agents may also be included; extemporaneous injection solutions and suspensions may be made from sterile powders, granules or tablets which may contain diluents, dispersing and surface active agents, binders and lubricants. The compound or salt may also be presented in suppositories or pessaries by incorporation in a suppository base.

It will be understood that the absolute quantity of compound or salt present in any discrete dosage unit should not exceed that appropriate to the rate and manner of administration to be employed, yet on the other hand should also desirably be adequate to allow the desired rate of administration to be achieved by a small number of dosage units, preferably a single one. The average rate of administration will, moreover, depend in particular on the actual compound or salt being presented. Nevertheless, in general it may be said that the preferred dosage range for an adult is from 2 to 500 mg., especially 5 to 200 mg., per day administered desirably at the most three times a day.

The present invention, in two further aspects, provides pharmaceutical compositions containing a compound of formula I or an acid addition salt thereof and an acceptable carrier therefor, and the method of making such compositions by bringing the components into association with each other.

Moreover, in a yet further aspect, the present invention provides a process for antagonising the physiological effects of 5-hydroxytryptamine which comprises administering a compound of formula I or an acid addition salt thereof.

The invention will now be described with reference to the following Examples, in which all temperatures are given in degrees Centigrade.

EXAMPLE 1

A mixture of phenylacetonitrile (3.5 g.) and 2-phenoxyethylamine p-toluenesulphonate (9.3 g.) was stirred and heated, in an oil-bath, to 270° for 1½ hours. The mixture was cooled somewhat and dissolved in ethanol (ca. 25 ml.), and the solution was poured into a mixture of water (150 ml.) and ether (150 ml.) which was shaken vigorously and then allowed to stand at room temperature. An oil, insoluble in ether and in water, slowly crystallised. The crystalline material was filtered, washed well with water and with ether and then extracted with two portions (150 ml.) of boiling water. On cooling, these extracts both deposited white crystals, m.p. 70°-73°; the two batches were combined and recrystallised from a mixture of ethanol and water to give N-(2-pnenoxyethyl)phenylacetamidine p-toluenesulphonate, m.p. 65°-70°, crystallising with 1½ mols of water of crystallisation.

EXAMPLE 2

A mixture of 2-phenoxypropylamine p-toluenesulphonate (3.7 g.) and phenylacetonitrile (1.5 g.) was stirred and heated, in an oil-bath, to 270° for 1½ hours. The mixture was cooled and dissolved in the minimum amount of boiling ethanol, and the solution was poured into a mixture of water (75 ml.) and ether (75 ml.). The mixture was shaken and the aqueous layer was separated, washed once with ether, and evaporated to half-volume under reduced pressure. An oil separated and crystallised after a few days. The product was filtered and recrystallised from water to give N-(2-phenoxypropyl)phenylacetamidine p-toluenesulphonate, m.p. 121°–124°.

EXAMPLES 3–18

These amidines, the melting points of which are given in Tables 1 and 2, were prepared by reaction between phenylacetamidino p-toluenesulphonate (prepared by method E below) and one equivalent of the corresponding primary amine, $R.NH_2$, in absolute ethanol. The mixture was heated to reflux until ammonia evolution had ceased (usually 3–4 hours), and was then diluted with ether or with water (indicated in Table 1) to precipitate the product.

The resulting amidines were recrystallised from the solvents indicated in the notes to the Tables and dried in a vacuum desiccator. In the indicated cases the products crystallised as hydrates which were dried at ambient temperature and pressure; all salts are anhydrous unless otherwise indicated. Column 3 of the Tables indicates the method A, B, C or D (given in detail below) used to prepare those primary amines hitherto undescribed; no entry in this column indicates that the amine is described in the literature. These considerations also apply to Tables 3–6.

The preparation of N-(2-phenoxypropyl)-phenylacetamidine p-toluenesulphonate (Example 3), given below, is typical. Examples 15–18 of Table 2 were prepared in the same manner but the reaction mixture was diluted with a saturated aqueous solution of 1:1 equivalents of sodium p-chlorobenzenesulphonate and the product was isolated as the p-chlorobenzenesulphonate salt.

2-Phenoxypropylamine (6.0 g.) was added to a suspension of phenylacetamidine p-toluenesulphonate (12.4 g.) in absolute ethanol (20 ml.). The mixture was heated to reflux for 4 hours by which time the initially vigorous evolution of ammonia had practically ceased. The resulting solution was cooled somewhat and diluted with ether to give an oil which rapidly crystallised on scratching. The solid was filtered and recrystallised from a mixture of ethanol and water to give N-(2-phenoxypropyl)phenylacetamidine p-toluenesulphonate, m.p. 127°–129°.

Table 1 p-Toluenesulphonate Salts of Amidines, $R.NH.\overset{NH}{\overset{\|}{C}}.CH_2.Ph$

| Example | R | Amino $RNH_2$, Method | Reaction mixture precip. with | M.p. | Crystallisation Solvent |
|---|---|---|---|---|---|
| 3 | 2-phenoxypropyl | B | ether | 127–129° | 3 |
| 4 | 2-benzyloxypropyl | D | ether | 89–91° monohydrate | 2 |
| 5 | 1-phenoxyprop-2-yl | — | water | 68–72° dihydrate | 3 |
| 6 | 2-phenoxybutyl | B | water | 106–109° | 4 |
| 7 | 2-(4-chloro-1-methylphenoxy)ethyl | A | water | 84–85° monohydrate | 2 |
| 8 | 2-3'-methylphenoxypropyl | B | water | 100–103° | 4 |
| 9 | 2-4'-methoxyphenoxypropyl | B | ether | 107–109° | 4 and 3 |
| 10 | 2-3'-methoxyphenoxypropyl | B | water | 93–96° | 6 |
| 11 | 2-3'-chlorophenoxypropyl | B | ether | 109–111° | 4 |
| 12 | 2-(3,5-dimethylphenoxy)-propyl | B | ether | 128–130° | 5 |
| 13 | 1-3'-methylphenoxyprop-2-yl | C | water | 46–50° monohydrate | 3 |
| 14 | 2-3'-ethoxyphenoxypropyl | B | ether with a few drops of water | 97–100° | 4 |

NOTE
The crystallisation solvents used in the Examples of Table 1, and subsequent Tables, are coded by the numbers 1 to 10. These numbers represent:
1. a mixture of ethanol and ether
2. a mixture of ethanol and ether together with a few drops of water
3. a mixture of ethanol and water
4. ethyl acetate
5. acetone
6. water
7. a mixture of acetone and water
8. isopropanol
9. benzene with a few drops of water
10. a mixture of isopropanol and water Table 2 p-Chlorobenzenesulphonate Salts of Amidines $R.NH.\overset{NH}{\overset{\|}{C}}.CH_2.Ph$

| Example | R | Amine $R.NH_2$, method | M.p. | Crystallization solvent* |
|---|---|---|---|---|
| 15 | 1-2'-methoxyphenoxyprop-2-yl | C | 85–87° anhydrous | 1 |
| 16 | 2-(4-chloro-3-methylphenoxy)propyl | B | 78–80° anhydrous | 1 |
| 17 | 2-3'-methylphenoxyethyl | A | 71–72° monohydrate | 4 |
| 18 | 2-3'-ethylphenoxyproply | B | 59–61° anhydrous | 7 and 3 |

*see footnotes to Table 1

Table 3

Hydrochlorides of Amidines, R.NH.C(=NH).CH$_2$.Ar

| Example | R | Amine R.NH$_2$, method | Ar | M.p. | Crystallization solvent* |
|---|---|---|---|---|---|
| 19 | 2-benzyloxypropyl | D | 2-chlorophenyl | 115–117° | 1 |
| 20 | 2-3'-methoxyphenoxyethyl | A | 4-chlorophenyl | 92–95° | 2 |
| 21 | 2-3'-methoxyphenoxypropyl | B | 2-chlorophenyl | 132–134° | 6 and 1 |
| 22 | 2-3'-methylphenoxypropyl | B | 2-chlorophenyl | 123–125° | 1 |
| 23 | 1-3'-methylphenoxyprop-2-yl | C | 4-chlorophenyl | 127–129° monohydrate | 1 and 5 |
| 24 | 2-3'-methoxyphenoxypropyl | B | 2,4-dichlorophenyl | 145–147° | 1 and 5 |

*see footnotes to Table 1

EXAMPLES 19–64.

The amidines of Tables 3, 4 and 5 were prepared by the reaction between a primary amine, R.NH$_2$, and one equivalent of an arylacetamidine hydrochloride,

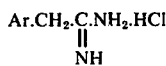

by the method of Example 3.
In Examples 19–24 of Table 3 the reaction mixture was diluted with ether to give the hydrochloride of the substituted amidine. In Examples 25–61 of Table 4 the reaction mixture was diluted with a saturated aqueous solution of 1.1 equivalents of sodium p-toluenesulphonate to give the p-toluenesulphonate salt. The amidines of Table 5, Examples 62–64, were precipitated as the p-chlorobenzenesulphonate salts in the usual manner.

The preparations of the intermediate amidine hydrochlorides,

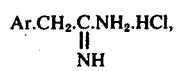

are described later under method F.

Table 4 p-Toluenesulphonate Salts of Amidines, R.NH.C(=NH).CH$_2$.Ar

| Example | R | Amine R.NH$_2$, method | Ar | M.p. | Crystallisation solvent |
|---|---|---|---|---|---|
| 23 | 2-phenoxypropyl | B | 4-methoxyphenyl | 156–158° | 1 |
| 26 | 2-phenoxypropyl | B | 2-chlorophenyl | 113–115° | 1 |
| 27 | 2-phenoxypropyl | B | 5,4-dimethoxyphenyl | 116–120° | 1 |
| 28 | 2-phenoxypropyl | B | 4-chlorophenyl | 165–167° | 3 |
| 29 | 2-3'-methylphenoxypropyl | B | 4-chlorophenyl | 144–146° | 7 |
| 30 | 2-3'-methoxyphenoxypropyl | B | 4-chlorophenyl | 121–123° | 4 |
| 31 | 2-3'-ethoxyphenoxypropyl | B | 4-chlorophenyl | 80–82° monohydrate | 2 |
| 32 | 2-(3,4-dimethylphenoxy)propyl | B | 4-chlorophenyl | 101–104° | 3 |
| 33 | 2-3'-ethylphenoxypropyl | B | 4-chlorophenyl | 115–117° | 1 |
| 34 | 2-(2,5-dimethylphenoxy)propyl | B | 4-chlorophenyl | 132–134° | 7, 4 and 1 |
| 35 | 2-phenoxypropyl | B | 2,4-dimethylphenyl | 142–144° | 3 and 1 |
| 36 | 2-2'-thenyloxypropyl | D | 4-chlorophenyl | 99–102° monohydrate | 3 and 1 |
| 37 | 2-phenoxypropyl | B | 2,4-dichlorophenyl | 154–156° | 1 |
| 38 | 2-phenoxypropyl | B | 4-bromophenyl | 165–167° | 4 and 5 |
| 39 | 2-phenoxybut-3-yl | C | 4-chlorophenyl | 155–157° | 1 and 5 |
| 40 | 2-phenoxypropyl | B | 3-methylphenyl | 120–122° | 1 and 4 |
| 41 | 2-3'-methoxyphenoxypropyl | B | 3-chlorophenyl | 63–65° monohydrate | 2 |
| 42 | 2-3'-methylbenzyloxypropyl | D | 4-chlorophenyl | 102–105° | 3, 1 and 4 |
| 43 | 2-3'-methylphenoxypropyl | B | 4-methoxyphenyl | 102–104° | 1, 4 and 7 |
| 44 | 2-3'-methylphenoxypropyl | B | 2,5-dimethylphenyl | 109–111° | 4 and 1 |
| 45 | 2-3'-methylphenoxypropyl | B | 3-methylphenyl | 112–113° | 3 and 1 |
| 46 | 1-3'-methoxyphenoxyprop-2-yl | C | 4-chlorophenyl | 88–89° monohydrate | 2 |
| 47 | 2-3'-chlorophenoxypropyl | B | 4-chlorophenyl | 153–155° | 1 |
| 48 | 2-3'-methylphenoxypropyl | B | 4-bromophenyl | 141–143° | 1 and 3 |
| 49 | 2-3'-methylphenoxypropyl | B | 3-chlorophenyl | 71–76° monohydrate | 7 |
| 50 | 2-3'-propoxyphenoxypropyl | B | 4-chlorophenyl | 88–89° monohydrate | 2, 3 and 7 |
| 51 | 2-3'-methoxyphenoxypropyl | B | 3-methylphenyl | 81–83° monohydrate | 2 and 4 |
| 52 | 2-phenoxypropyl | B | 3-methoxyphenyl | 113–116° | 1 and 4 |
| 53 | 2-3'-methoxyphenoxypropyl | B | 3-methoxyphenyl | 55–60° monohydrate | 3 |
| 54 | 2-3'-methylphenoxy-but-3-yl | C | 4-chlorophenyl | 71–74° monohydrate | 3 |
| 55 | 2-3'-methoxyphenoxypropyl | B | 4-bromophenyl | 119–121° | 1 and 4 |
| 56 | 1-phenoxyprop-2-yl | — | 3-methylphenyl | 108–111° | 4 and 1 |
| 57 | 2-2'-thenyloxypropyl | D | 3-methylphenyl | 104–106 | 1, 4 and 3 |
| 58 | 2-(3,5-dimethoxyphenoxy)-propyl | B | 3-methylphenyl | 143–144° | 3 and 8 |
| 59 | 2-3'-chlorophenoxyethyl | A | 4-chlorophenyl | 96–97° monohydrate | 3 |
| 60 | 2-3'-methoxyphenoxypropyl | B | 3,5-dimethylphenyl | 91–93° monohydrate | 4 and 2 |
| 61 | 2-(3-methoxy-5-methylphenoxy)propyl | B | 3-methylphenyl | 92–94° monohydrate | 10 |

*see footnotes to Table 1

Table 5 p-Chlorobenzenesulphonate Salts of Amidines, $R.NH.\overset{NH}{\overset{\|}{C}}.CH_2.Ar$.

| Example | R | Amine R.NH$_2$, Method | Ar | M.p. | Crystal- lisa- tion solvent* |
|---|---|---|---|---|---|
| 62 | 2-phenoxypropyl | 3 | 2-thienyl | 102–103° | 4 and 3 |
| 63 | 2-3'-methylphenoxyethyl | A | 3-methylphenyl | 70–72° monohydrate | 7 and 9 |
| 64 | 2-3'-methoxyphenoxyethyl | A | 3-methylphenyl | 73.5–76° monohydrate | 3 and 9 |

*see footnotes to Table 1

Examples 65–75

These amidines were prepared by the reaction between a primary amine, R.NH$_2$, and one equivalent of the p-toluenesulphonate salt of an amidine,

as described for Example 3. The reaction mixture was diluted with water (ether in the case of Example 65) to give the substituted amidine p-toluenesulphonate.

(30 ml.) was stirred and heated in an oil-bath. The bath temperature was raised slowly to 140° and maintained at that temperature for 30 minutes. The reaction mixture was poured into water and the precipitated solid was removed and dried. One recrystallisation from isopropanol gave the phthalimide derivative, m.p. 138°.

A suspension of the phthalimide derivative (40.2 g.) in boiling ethanol (250 ml.) was treated with hydrazine hydrate (19.2 g.) and heated to reflux. During the first 10 minutes of heating the solid dissolved and a second, voluminous solid was precipitated. Heating was continued for a total of 3 hours; the mixture was then treated cautiously with concentrated hydrochloric acid (40

Table 6 p-Toluenesulphonate Salts of Amidines, $R.NH.\overset{NH}{\overset{\|}{C}}.CH_2.Ar$

| Example | R | Amine, R.NH$_2$, method | Ar | M.p. | Crystallisation solvent * |
|---|---|---|---|---|---|
| 65 | 2-3'-methoxyphenoxypropyl | B | 4-fluorophenyl | 113–115° | 3 and 1 |
| 66 | 2-phenoxypropyl | B | 4-methylphenyl | 168–170° | 1 and 7 |
| 67 | 2-3'-methylphenoxypropyl | B | 2-methylphenyl | 98–101° | 4 and 1 |
| 68 | 2-3'-methylphenoxypropyl | B | 4-methylphenyl | 104–106° | 4 and 1 |
| 69 | 2-3'-methoxyphenoxypropyl | B | 3,4-dimethylphenyl | 123–124° | 1 and 3 |
| 70 | 2-phenoxypropyl | B | 3,4-dimethylphenyl | 112–116° | 4, 1 and 3 |
| 71 | 3-3'-methoxyphenoxypropyl | A | 3,4-dimethylphenyl | 74.5–76°, monohydrate | 2 and 7 |
| 72 | 2,3'-methylphenoxypropyl | B | 3,4-dimethylphenyl | 65–70°, monohydrate | 3 |
| 73 | 4-3'-methoxyphenoxybutyl | A | 3,4-dimethylphenyl | 101–103° | 9 |
| 74 | 2-2'-thenyloxypropyl | D | 3,4-dimethylphenyl | 126–131° | 1 and 7 |
| 75 | 1-3'-methoxyphenoxyprop-2-yl | C | 3,4-dimethylphenyl | 60–63° monohydrate | 3 |

* see footnotes to Table 1

Preparation of Intermediate Amines: Method A.

A mixture of 4-chloro-3-methylphenol (100 g.) and 1,2-dibromoethane (158.2 g.) in water (160 ml.) was stirred and heated to reflux during the slow dropwise addition of a solution of sodium hydroxide (30.8 g.) in water (140 ml.). Stirring and heating were continued for a total of 6 hours and the mixture was cooled and extracted exhaustively with ether. The ethereal extract was washed exhaustively with 5N-sodium hydroxide, dried over potassium carbonate, filtered and evaporated. The residual oil was distilled under reduced pressure to give 1-bromo-2-(4-chloro-3-methylphenoxy)ethane, b.p. 106°–112°10.65 mm.

A mixture of this bromo-compound (40 g.) and potassium phthalimide (29.7 g.) in dimethylformamide (30 ml.) heated on the steam-bath for 15 minutes, cooled and filtered. The precipitate was washed well with water, and the combined filtrate and washings were evaporated under reduced pressure to remove most of the ethanol. The residue was diluted with water, and made strongly basic with sodium hydroxide. The precipitated oil was isolated with ether in the usual manner in give 2-(4-chloro-3-methylphenoxy)ethylamine, b.p. 97–99°/0.2 mm.

The following primary aryloxyalkylamines, the boiling points of which are given in Table 7, were prepared essentially by the same methods. Table 7 also gives the boiling-points of the intermediate bromo-comound and the melting-points of the corresponding phthalimide derivatives.

Table 7

Intermediate amines, R.NH$_2$

R.N(CO-)(CO-) [phthalimide structure with benzene ring]

| R | R.Br b.p. | m.p. | R.NH$_2$ b.p. |
|---|---|---|---|
| 2-3'-methoxyphenoxyethyl | 160–174°/12 mm. | 114–115° | 152–154°/12 mm. |
| 2-3'-methylphenoxyethyl | 139–142°/13 mm. | 99–101° | 130–132°/13 mm. |
| 2-3'-chlorophenoxyethyl | 143–140°/12 mm. | 85–87° | 148–150°/16 mm. |
| 3-3'-methoxyphenoxypropyl | 171–175°/15 mm.x | 102–104° | 164–165°/13 mm. |
| 4-3'-methoxyphenoxybutyl | 124–126°/0.03 mm.xx | 91–92° | 189–191°/24 mm. | x This bromo-compound was prepared as follows: 3-Methoxyphenol (49.6 g.) was added to a solution of sodium (9.2 g.) in ethanol (400 ml.). 1,3-Dibromopropane (121 g.) was added with stirring and the mixture was heated to reflux for 2 hours. Water (1 l.) was added to the cooled mixture which was then extracted with ether. The ether extract was washed with water and with 2N-sodium hydroxide, dried over sodium sulphate and distilled. xx This compound was prepared in a similar manner, starting from 3-methoxyphenol, and using 1,4-dibromobutane in place of 1,3-dibromopropane.

Preparation of Intermediate Amines: Method B.

A mixture of phenol (18.8 g.) and anhydrous potassium carbonate (25 g.) in dry ethyl methyl ketone (35 ml.) was stirred and heated to reflux, during the dropwise addition of a solution of 2-chloropropionitrile (19.7 g.) in dry ethyl methyl ketone (15 ml.) containing finely-powdered potassium iodide (0.5 g.). The addition took 20 minutes. Stirring and heating were continued for a total of 2 hours after which the mixture was cooled, poured into water (200 ml.) and extracted with ether (200, 75 and 75 ml.). The combined ether extract was washed several times with 2N-sodium hydroxide to remove phenol, dried over anhydrous sodium sulphate, and evaporated. The residue was distilled under water-pump vacuum to give pure 2-phenoxypropionitrile, b.p. 117°–118°/13 mm.

A solution of 2-phenoxypropionitrile (11.0 s.) in dry ether (50 ml.) was added dropwise to a stirred suspension of lithium aluminium hydride (3.8 g.) in dry ether (50 ml.). The mixture was then heated to reflux for 3 hours, cooled and treated cautiously (vigorous stirring) with water (3.8 ml.) then with 15% aqueous sodium hydroxide (3.8 ml.) and finally with water (11.4 ml.). The mixture was stirred for 20 minutes and filtered. The filtrate was dried over anhydrous potassium carbonate and evaporated. The residue was distilled under water-pump vacuum to give pure 2-phenoxypropylamine, b.p. 115°–116°/15 mm.

The primary amines of the last column in Table 8 were also prepared by Method B. Table 8 gives the boiling-points of the intermediate nitriles as well as of the amines.

Table 8

| | Boiling points | |
|---|---|---|
| Ar | Ar.O.CH(CH$_3$).CN | Ar.O.CH(CH$_3$).CH$_2$.NH$_2$ |
| 3-methylphenyl | 125–128°/12 mm. | 120–124°/15 mm. |
| 2-methoxyphenyl | 153–154°/16 mm. | 142–144°/20 mm. |
| 4-chloro-3-methylphenyl | 164–218°/25 mm. | 148–150°/23 mm. |
| 4-methylphenyl | 123–127°/12 mm. | 126–127°/14 mm. |
| 5-methoxyphenyl | 152–154°/13 mm. | 148–152°/13 mm. |
| 3-chlorophenyl | 138–142°/13 mm. | 136–138°/13 mm. |
| 2,5-dimethylphenyl | 142–144°/14 mm. (m.p. 53–54°) | 134–137°/13 mm. |
| 3-ethoxyphenyl | 158–162°/14 mm. | 156–138°/12 mm. |
| 3,4-dimethylphenyl | 144–146°/13 mm. | 138–140°/13 mm. |
| 3-ethylphenyl | 134–136°/12 mm. | 133–135°/12 mm. |
| 2,5-dimethylphenyl | 132–135°/13 mm. | 131–134°/14 mm. |
| 3,5-dimethoxyphenyl | 181–184°/17 mm. | 184–186°/16 mm. |
| 3-methoxy-5-methylphenyl | 164–166°/13 mm. | 162–164°/17 mm. |
| 3-propoxyphenyl | 172–178°/15 mm. | x | x This amine was not distilled. The total crude reaction product from lithium aluminium hydride reduction of the nitrile was used to prepare the amidine, Example 50.

| | Boiling points | |
|---|---|---|
| Ar | Ar.O.CH(CH$_2$.CH$_3$).CN | Ar.O.CH(CH$_2$.CH$_3$).CH$_2$.NH$_2$ |
| Phenyl | 126–127°/13 mm. | 124–128°/13 mm. |

Preparation of Intermediate Amines: Method C (i).

A mixture of chloroacetone (43.75 g.) and finely-powdered potassium iodide (1 g.) in ethyl methyl ketone (50 ml.) was added dropwise, over 25 minutes, to a stirred, refluxing mixture of 3-methylphenol (54 g.) and dry potassium carbonate (82 g.) in ethyl methyl ketone (100 ml). Stirring and refluxing were continued for a total of 5 hours and the mixture was cooled, poured into water (cs. 500 ml.) and extracted with ether. The ether extract was washed exhaustively with 5N-sodium hydroxide, dried over anhydrous sodium sulphate and evaporated. The residue was distilled to give a fraction b.p. 126°–134°/13 mm. Redistillation gave 1-(3-methylphenoxy)-propan-2-one, b.p. 124°–126°/13 mm.

1-(3-Methylphenoxy)propan-2-one (24.9 g.) and ethanol (100 ml.) were added to a solution of hydroxylamine hydrochloride (25 g.) and fused sodium acetate (25 g.) in water (110 ml.). The resulting solution was refluxed for 3½ hours and evaporated to near dryness under reduced pressure. The residue was partitioned between water and ether. The ether extract was washed with water, dried over anhydrous potassium carbonate and evaporated. The residue was distilled to give a fraction, b.p. 159°–163°/12 mm. Redistillation gave 1-(3-methylphenoxy)propan-2-one oxime, b.p. 165°–167°/13 mm.

A solution of 1-(3-methylphenoxy)propan-2-one oxime (13.7 g.) in dry ether (100 ml.) was added dropwise, over 45 minutes, to a stirred, refluxing mixture of lithium aluminium hydride (5.85 g.) in dry ether (200 ml.). Stirring and heating were continued for 4 hours and the mixture was cooled and treated cautiously with water (5.8 ml.) followed by 15% aqueous sodium hydroxide (5.8 ml.), and finally, water (17.5 ml.). The mixture was stirred for 30 minutes and then filtered. The filtrate was dried over anhydrous potassium carbonate and evaporated. The residue was distilled to give 1-(3-methylphenoxy)prop-2-ylamine, b.p. 124°–128°/13 mm.

The following two amines were also prepared by method C (i):

1-(2-Methoxyphenoxy)prop-2-ylamine, b.p. 146°–148°/17 mm. The intermediate ketone had b.p. 142°–149°/12–15 mm. (m.p. 35°–38°) and the derived oxide m.p. 82°–84°.

1-(3-Methoxyphenoxy)prop-2-ylamine, b.p. 152°–157°/13 mm. The intermediate ketone had b.p. 158°–164°/17 mm. and the derived oxime b.p. 176°–186°/13 mm.

Preparation of Intermediate Amines: Method C (ii).

A mixture of 3-bromobutan-2-one (75.5 g.) and finely-powdered potassium iodide (1 g.) in ethyl methyl ketone (50 ml.) was added dropwise, over 25 minutes, to a stirred, refluxing mixture of phenol (47 g.) and dry potassium carbonate (82 g.) in ethyl methyl ketone (100 ml.) Stirring and refluxing were continued for a total of 5 hours and the mixture was cooled, poured into water (cs. 500 ml.) and extracted with ether. The ether extract was washed exhaustively with 5N-sodium hydroxide, dried over anhydrous sodium sulphate and evaporated. The residue was distilled to give pure 3-phenoxybutan-2-one, b.p. 110°–112°/14 mm.

3-Phenoxybutan-2-one (69.6 g.) and ethanol (300 ml.) were added to a solution of hydroxylamine hydrochloride (70 g.) and fused sodium acetate (70 g.) in water (130 ml.). The resulting solution was refluxed for 3½ hours and evaporated to near dryness under reduced pressure. The residue was partitioned between water and ether. The ether extract was washed with water, dried over anhydrous potassium carbonate and evaporated. The residue was distilled to give a fraction, b.p. 154°–155°/14 mm. which crystallised. Recrystallisation from petroleum ether (b.p. 60°–80°) gave pure 3-phenoxybutan-2-one oxime, m.p. 65°–67°.

A solution of 3-phenoxybutan-2-one oxime (28.8 g.) in dry ether (150 ml.) was added dropwise, over 45 minutes, to a stirred, refluxing mixture of lithium aluminium hydride (6.3 g.) in dry ether (100 ml.). Stirring and heating were continued for 4 hours and the mixture was cooled and treated cautiously with water (6.3 ml.) followed by 15% aqueous sodium hydroxide (6.3 ml.), and finally, water (18.9 ml.). The mixture was stirred for 30 minutes and then filtered. The filtrate was extracted with 2N-hydrochloric acid (150 ml.) and the acid extract was made strongly basic with sodium hydroxide and extracted with ether. The ether extract was dried over anhydrous potassium carbonate, evaporated, and distilled to give a fraction, b.p. 118°–124°/14 mm. Redistillation gave pure 2-phenoxybut-3-ylamine, b.p. 116°–118°/14 mm.

Also by Method C (ii) was prepared 2-3'-methylphenoxybut-3-ylamine, b.p. 128°–130°/15 mm. The intermediate ketone had b.p. 120°–122°/14 mm. and the derived oxime had b.p. 161°–162°/13 mm.

Preparation of Intermediate Amines: Method D.

Freshly distilled 2-aminopropanol (60 g.) was stirred and heated gently during the portionwise addition of sodium (16.1 g.). Stirring and heating were continued until all the sodium had reacted, and toluene (100 ml.) was added. The mixture was then heated to gentle reflux and treated dropwise, over 1 hour, with benzyl chloride (50 g.). Heating was continued for a further 4 hours, and the mixture cooled and filtered, and the precipitate washed with toluene. The combined filtrate and washings were washed four times with water, dried over anhydrous potassium carbonate, and evaporated. The residue was distilled under oil-pump vacuum to give three fractions as follows:

Fraction (1), b.p. 58°–61°/0.03 mm.
Fraction (2), b.p. 70°–72°/0.03 mm.
Fraction (3), b.p. 72°–92°/0.03 mm.

Fractions (1) and (2) were combined and redistilled to give pure 2-benzyloxypropylamine, b.p. 72°–74°/0.15 mm.

In essentially the same manner the reaction between 2-aminopropanol and 3-methylbenzylbromide gave a fraction, b.p. 139°–143°/14 mm. which was redistilled to give pure 2-3'-methylbenzyloxypropylamine, b.p. 135°–136°/13 mm.

The reaction between 2-aminopropanol and thenyl chloride gave 2-2'-thenyloxypropylamine, b.p. 69°–71°/0.1 mm.

Preparation of Intermediate Amidines: Method E.

A mixture of 4-fluorophenylacetonitrile (71 g.) and dry ethanol (27.6 g.) was cooled in an ice-bath and dry hydrogen chloride was passed in until a weight increase of 25.5 g. was obtained. The mixture was allowed to stand at room temperature for 3 days and then treated portionwise, with vigorous shaking and occasional cooling, with a saturated solution of ammonia in dry ethanol. Addition was continued until a smell of ammonia persisted. The mixture was allowed to stand at room temperature for 2 days and then filtered. The filtrate was treated with a saturated aqueous solution of 1.1 equivalents of sodium p-toluenesulphonate and diluted with water. The crystalline precipitate was removed and recrystallised from ethanol to give pure 4-fluorophenylacetamidine p-toluenesulphonate, m.p. 215°–218°. The following amidines were also prepared by Method E; crystallisation solvents are given in brackets:

Phenylacetamidine p-toluenesulphonate, mp. 196°–198° (ethanol).

4-Methylphenylacetamidine p-toluenesulphonate, m.p. 227°–230° (mixture of ethanol and water).

2-Methyl phenylacetamidine p-toluenesulphonate, m.p. 138°–139° (ethanol).

3,4-Dimethyl phenylacetamidine p-toluenesulphonate, m.p. 176°–178° (mixture of ethanol and ether).

Preparation of Intermediate Amidines: Method F

Dry hydrogen chloride was passed into a mixture of 3-methoxyphenylacetonitrile (19.7 g.) and dry ethanol (6.8 g., 7.8 ml.) until a weight increase of 5 g. was obtained. The mixture was allowed to stand at room temperature for 3 days and the solid mass was broken up and treated portionwise, with vigorous shaking and occasional cooling, with a saturated solution of ammonia in dry ethanol. Addition was continued until a smell of ammonia persisted. The mixture was allowed to stand at room temperature for 2 days and then warmed and filtered to remove a small amount of ammonium chloride. The filtrate was diluted with ether and the crystalline precipitate was removed and recrystallised from a mixture of ethanol and ether to give pure 3-methoxy-phenylacetamidine hydrochloride, m.p. 142°–144°.

The following arylacetamidines (Table 9) were also prepared essentially by the Method F.

Table 9

Arylacetamidine hydrochlorides, $Ar.CH_2.\overset{NH}{\underset{\|}{C}}.NH_2.HCl$

| Ar | M.p. | Crystallisation solvent* |
|---|---|---|
| 4-Bromophenyl | 203–204° | 1 |
| 3-Chlorophenyl | 194–196° | 1 |
| 3-Methylphenyl | 166–167° | 1 |
| 2,4-Dichlorphenyl | 193–195° | 1 |
| 2,5-Dimethylphenyl | 145–147° | 7 |
| 4-Chlorophenyl | 188–189° | ethanol |
| 4-Methoxyphenyl | 90–92° monohydrate | 2 |
| 2,4-Dimethylphenyl | 132–134° | 5 |
| 2-Chlorophenyl | 135–137° hemihydrate | 1 |
| 3,4-Dimethoxyphenyl | 170–172° | ethanol |
| 2-Thienyl | 110–114° | 1 |
| 3,5-Dimethylphenyl | 217–219° | 1 and 7 |

*see footnotes to Table 1

EXAMPLE 76

A saturated aqueous solution of 4-chlorophenylacetamidine hydrochloride was treated with an excess of 10N-aqueous sodium hydroxide with rapid stirring and ice-cooling. The crystalline precipitate was immediately filtered, washed with water and dried in vacuo. The resulting 4-chlorophenylacetamidine base (1.7 g.) in dry benzene (5 ml.) was treated with 2-phenoxypropylamine (1.5 g.) and the solution was heated to reflux. Nitrogen was bubbled through the refluxing solution and then passed through N-sulphuric acid to absorb the ammonia evolved. After 3 hours 20 minutes the theoretical amount of ammonia had been evolved and the reaction mixture was cooled and treated with a solution of p-toluene-sulphonic acid (1.8 g.) in a little ethanol. The solution was diluted with ether and the crystalline solid was filtered and dried. One recrystallisation from a mixture of ethanol and ether gave N-(2-phenoxy-propyl)-4-chlorophenylacetamidine p-toluenesulphonate, m.p. 167°–169°, undepressed on admixture with the product of Example 28.

EXAMPLE 77

Dry hydrogen chloride was passed into a mixture of 4-chlorophenylacetonitrile (50.5 g.) and dry ethanol (16.1 g., 20.1 ml.) until a weight increase of 14.6 g. was obtained. The mixture was allowed to stand at room temperature for 3 days; the resulting crystalline mass was broken up, digested thoroughly with dry ether, filtered, and dried in vacuo to give ethyl 4-chlorophenylacetimidate hydrochloride.

A portion of this imide-ester hydrochloride (2.34 g.) was suspended in dry ethanol (10 ml.) and treated dropwise (swirling) with a solution of 2-phenoxypropylamine (1.5 g.) in dry ethanol (5 ml.). The mixture was shaken for a few minutes until homogeneous, allowed to stand for 2 hours at room temperature, and then treated with 2N-aqueous sodium p-toluenesulphonate (6 ml.). After 1 hour at room temperature the crystalline precipitate was filtered and dried in vacuo to give a product, m.p. 151°–155°. One recrystallisation from a mixture of ethanol and water, followed by recrystallisation from a mixture of ethanol and ether, gave N-(2-phenoxy-propyl)-4-chlorophenylacetamidine p-toluenesulphonate, m.p. 162°–163.5°, undepressed on admixture with the product of Example 28.

EXAMPLE 78

A solution of 4-chlorophenyl(thioacetamide) (14.8 g.) and methyl iodide (32 g.) in acetone (40 ml.) was heated to reflux for 20 minutes. The mixture was cooled and filtered to give pure methyl 4-chlorophenyl(thioacetimidate) hydriodide, m.p. 172°–174°.

This imido-thioester hydriodide (3.7 g.) was added to a solution of 2-3'-methylphonoxypropylamine (1.7 g.) in dry ethanol (5 ml.); there was a slight exothermic reaction. The solution was allowed to stand at room temperature for 2 hours, heated to reflux to expel methyl mercaptan, and diluted with ether. The precipitated product, m.p. 151°–152°, was recrystallised from a mixture of acetone and water to give N-(2-3'-methylphenoxypropyl)-4-chlorophenylacetamidine hydriodide, m.p. 152°–154°.

EXAMPLE 79

The reaction between methyl 4-chlorophenyl(thioacetimidate)hydriodide (3.7 g.) and 2-3'-methylphenoxypropylamine (1.7 g.) was carried out as in Example 78, except that the reaction solution was diluted, not with ether, but with 2N-aqueous sodium p-toluenesulphonate (5.5 ml.) followed by water. The resulting crystalline product was recrystallised from a mixture of ethanol and ether, and then from a mixture of acetone and water, to give N-(2-3'-methylphenoxypropyl)-4-chlorophenylacetamidine p-toluenesulphonate, m.p. 145°–147°, undepressed on admixture with the product of Example 29.

EXAMPLE 80

The reaction between methyl 4-chlorophenyl(thioacetimidate) hydriodide (3.7 g.) and 1-3'-methoxyphenoxyprop-2-ylamine (1.8 g.) was carried out exactly as in Example 79. The product was recrystallised from a mixture of ethanol and other containing a little water to give N-(1-3'-methoxyphenoxyprop-2-yl)-4-chlorophenylacetamidine p-toluenesulphonate monohydrate, m.p. 88°–89°, undepressed on admixture with the product of Example 46.

EXAMPLE 81

A mixture of 4-chlorophenyl(thioacetamide) (1.9 g.) and 2-3'-methylphenoxypropylamine (1.7 g.) in ethanol (5 ml.) was heated to reflux for 5 hours, during which time both ammonia and hydrogen sulphide were evolved. The reaction solution was evaporated to dryness under reduced pressure, and the residue was dissolved in 2H-hydrochloric acid and treated with 2N-aqueous sodium p-toluenesulphonate (5.5 ml.); an oil was precipitated. The supernatant solution was decanted and the oil was triturated with ether to give a crystalline product, m.p. 141°–145°. One recrystallisation from a mixture of acetone and water, followed by one from a mixture of ethanol and ether, gave N-(2-3'-methylphenoxypropyl)-4-chlorophenylacetamidine p-toluenesulphonate, m.p. 145°–146°, undepressed on admixture with the product of Example 29.

EXAMPLE 82

Equal weights of 2-3'-methoxyphenoxypropylamine and p-toluenesulphonic acid were mixed together in ethanolic solution, and the mixture was then diluted with ether. The precipitated salt, 2-3'-methoxyphenoxypropylamine p-toluenesulphonate, had m.p. 96°–97.5° after recrystallisation from a mixture of acetone and ether.

A mixture of 4-chlorophenyl(thioacetamide) (1.9 g.) and 2-3'-methoxyphenoxypropylamine p-toluenesulphonate (3.5 g.) in ethanol (5 ml.) was heated to reflux for 5 hours. Hydrogen sulphide was evolved during this time but no ammonia could be detected. The reaction solution was diluted with water to give an oil which slowly crystallised. After 3 days the crystalline material, containing some unreacted thioamide, was filtered, dried in vacuo, and dissolved in ethyl acetate (10 ml.). The solution was left at 0°. After several days a crystalline product, m.p. 118°–121°, was obtained. Recrystallisation from a mixture of ethanol and ether gave N-2-3'-methoxyphenoxypropyl)-4-chloro-phenylacetamidine p-toluenesulphonate, m.p. 124°–125°, undepressed on admixture with the product of Example 30.

EXAMPLE 83

Hydrogen sulphide gas was passed through a solution of 3-methylphenylacetonitrile (26.2 g.) in dry pyridine (30 ml.) and triethylamine (20.2 g.) during 5 hours. The solution was allowed to stand at room temperature overnight and then evaporated under reduced pressure. The residue was dissolved in benzene and precipitated with light petroleum (b.p. 60°–80°). The product, m.p. 66°–69°, was recrystallised from a mixture of ethanol and water to give pure 3-methylphenyl(thioacetamide), m.p. 76°–78°.

A solution of 3-methylphenyl(thioacetamide) (4.9 g.) and methyl iodide (12.6 g.) in acetone (15 ml.) was heated to reflux for 20 minutes. The mixture was cooled and filtered to give pure methyl 3-methylphenyl(thioacetimidate) hydriodide, m.p. 142°–144°.

The reaction between this imido-thioester hydriodide (3.1 g.) and 2-3'-methoxyphenoxypropylamine (1.8 g.) was carried out by the method of Example 78. The product was recrystallised from ethyl acetate to give N-(2-3'-methoxyphenoxypropyl)-3-methyl-phenylacetamidine hydriodide, m.p. 118°–120°.

EXAMPLE 84

A mixture of 4-chlorophenyl(thioacetamide) (1.8 g.) and methyl p-toluenesulphomate (1.8 g.) was heated on the steam-bath for 10 minutes. the clear melt was dissolved in ethanol (5 ml.) and treated with 2-3'-methylphenoxypropylamine (1.7 g.). The solution was heated to reflux for 15 minutes, cooled and diluted with ether to give a crystalline product. One recrystallisation from a mixture of acetone and water gave N-(2-3'-methylphenoxypropyl)-4-chlorophenylacetamidine p-toluenesulphonate, m.p. 144°–145°, undepressed on admixture with the product of Example 29.

This melt could be triturated with acetone to give crystalline methyl 4-chlorophenyl (thioacetimidate) p-toluenesulphonate, m.p. 127-130°.

EXAMPLE 85

2-Phenoxypropylamine (4.6 g.) was added to a mixture of phenylacetyl chloride (4.6 g.) and anhydrous sodium carbonate (3.3 g.) in dry benzene (20 ml.); there was an exothermic reaction and effervescence. The mixture was heated to reflux for 1 hour, cooled, treated with water, and then shaken. The benzene layer was separated, dried over anhydrous sodium sulphate, filtered, and diluted with light petroleum (b.p. 60°–80°) to give pure N-(2-phenoxypropyl) phenylacetamide, m.p. 94°–96°.

A mixture of this amide (1.7 g.) and phosphorus pentachloride (1.4 g.) was heated on the steam-bath for 10 minutes. The clear melt was evaporated, first on the waterpump, and then under oil-pump vacuum, at ca. 60° to remove phosphorus oxychloride. The residue, crude imidyl chloride, was treated with saturated ethanolic ammonia (ca. 5 ml) and the mixture was shaken, thoroughly mixed and then warmed on the steam-bath for 15 minutes. In another procedure, the crude imidyl chloride was dissolved in benzene and treated with gaseous ammonia for 10 minutes after which the solution was evaporated to dryness and the residue dissolved in water. In each case, the resulting solution was cooled and treated with 2N-aqueous sodium p-toluenesulphonate (3.5 ml.), followed by water (10 ml.), to precipitate an oil. The supernatant solution was decanted and the oil was washed with water, then three times with ether, and finally dissolved in a little ethyl acetate. After a few hours at 0° the solution deposited a crystalline material, m.p. 121°–125°. Recrystallisation from a mixture of ethanol and water gave N-(2-phenoxypropyl)phenyl acetamidine p-toluenesulphonate, m.p. 124°–127°, underpressed on admixture with the product of Example 3. The ethyl actate mother liquor deposited a further amount of purer material, m.p. 127°–129°.

EXAMPLE 86

Tablets (0.555 g.) were made by mixing N-(2-3'-methoxyphenoxypropyl)-4-chlorophenylacetamidine (0.25 g.), in a fine powder with lactose (0.25 g.) and starch (0.05 g.), granulating the mixture with alcohol, or alcoholic polyvinyl pyrrolidone, or a mixture of equal parts of alcohol and water, drying the granules at 40°, adding magnesium stearate (0.005 g.) as a lubricant, and compressing the mixture directly.

EXAMPLE 87

Tablets (0.505 g.) were made by granulating N-(2-3'-methoxyphenoxypropyl)-4-chlorophenylacetamidine, p-toluenesulphonate (0.5 g.) in a fine powder with equal parts of alcohol and water, adding magnesium stearate (0.005 g.) as a lubricant, and compressing the mixture directly.

EXAMPLE 88

Tablets similar to those described in Examples 86 and 87 were made using N-(2-3'-methylphenoxypropyl)-4-chlorophenylacetamidine p-toluenesulphonate instead of the 3-methoxy compound.

EXAMPLE 89

Tablets similar to those described in Examples 86 and 87 were made using, instead of the 3-methoxy compound. N-(2-3'-methoxyphenoxypropyl)-3-methylphenylacetamidine or N-(2-3'-methoxyphenoxypropyl)-3,4-dichlorophenylacetamidine or a salt thereof.

EXAMPLE 90

Aluminum chloride (1.3 g.) was added to stirred mixture of 2-3'-methylphenoxypropylamine (1.7 g.) and 4-chlorophenylacetonitrile (1.5 g.). There was an exothermic reaction, and the mixture was then heated to 160° for 30 minutes, cooled, and poured into 2N-hydrochloric acid (20 ml.) with vigorous stirring. The resulting mixture was made strongly basic with 10N-sodium hydroxide and extracted with ether. The ether extract was dried over anhydrous potassium carbonate and evaporated; the residue was dissolved in 2N-hydrochloric acid and treated with 2N-aqueous sodium p-toluenesulphonate (5.5 ml.). The supernatant aqueous solution was decanted off the resulting oil, which was washed first with water and then three times with ether, and finally triturated with ethyl acetate. The crystalline product was recrystallised from a mixture of acetone and water to give N-(2-3'-methylphenoxypropyl)-4-chlorophenylacetamidine p-toluenesulphonate, m.p. 142°–144°, undepressed on admixture with the product of Example 29.

EXAMPLE 91

A solution of 2-chloropropionitrile (26.85 g.) in dry ethyl methyl ketone (40 ml.) containing finely powdered potassium iodide (0.5 g.) was added dropwise, over 15 minutes, to a stirred, refluxing mixture of 2-benzyloxyphenol (60 g.) and anhydrous potassium carbonate (41.4 g.) in dry ethyl methyl ketone (60 ml.) The mixture was then stirred and refluxed for 4 hours, cooled and poured into water (300 ml.), and the aqueous mixture was extracted with ether. The extract was dried over potassium carbonate and evaporated. The residue was distilled to give 2-2'-benzyloxyphenoxypropionitrile, b.p. 143°–149°/0.08 mm.

A solution of 2-2'-benzyloxyphenoxypropionitrile (23.9 g.) in dry ether (100 ml.) was added dropwise, over 40 minutes, to a stirred, refluxing suspension of lithium aluminium hydride (3.8 g.) in dry ether (150 ml.). The mixture was then stirred and refluxed for 4 hours, cooled, and treated successively with water (3.8 ml.), 15% aqueous sodium hydroxide (3.8 ml.), and water (11.4 ml.). Finally the mixture was stirred for 30 minutes and filtered. The filtrate was dried over potassium carbonate and evaporated. The residual oil was distilled to give 2-2'-benzyloxyphenoxypropylamine, b.p. 148°–152°/0.07 mm.

A mixture of 2-2'-benzyloxyphenoxypropylamine (5.85 g.) and 4-chlorophenylacetamidine hydrochloride (4.7 g.) in ethanol (20 ml.) was refluxed for 2½ hours. The solution was treated with 2N aqueous sodium p-toluenesulphonate (12 ml.) and the mixture evaporated to dryness under reduced pressure. The residue was extracted with hot water (30 ml.), which removed a small amount of 4-chlorobenzylacetamidine p-toluenesulphonate, and then dissolved in warm ethanol and treated with ether until the solution became turbid. The solution was allowed to stand overnight and the resulting crystalline product was filtered and dried in vacuo. Two recrystallisations from a mixture of ethanol and ether gave pure N-(2-2'-benzyloxyphenoxypropyl)-4-chlorophenylacetamidine p-toluenesulphonate, m.p. 119°–120°.

EXAMPLE 92

Essentially by the methods of Example 1, 3-benzyloxyphenol was converted to 2-3'-benzyloxyphenoxypropionitrile, b.p. 152°–156°/0.05 mm., and thence to 2-3'-benzyloxyphenoxypropylamine, b.p. 154°–156°/0.03 mm.

A mixture of 2-3'-benzyloxypropylamine (2.6 g.) and 3-methylphenylacetamidine hydrochloride (1.85 g.) in ethanol (10 ml.) was heated to reflux for 4 hours. The product could not be crystallised and the total reaction mixture, containing N-(2-3'-benzyloxyphenoxypropyl)-3-methylphenylacetamidine hydrochloride, was used for biological testing.

EXAMPLE 93

By the method of the first part of Example 1, m-hydroxybiphenyl (m-phenylphenol) was converted to 2-3'-phenylphenoxypropionitrile, b.p. 143°–145°/0.5 mm., m.p. 55°–58° after recrystallisation from a mixture of benzene and light petroleum (b.p. 60.80°). This nitrile was reduced with lithium aluminium hydride and ether, also as described in Example I, to give 2-3'-phenylphenoxypropylamine, b.p. 208°–209°/13 mm.

A mixture of 3,4-dimethylphenyl(thioacetamide) (1.8 g.) and methyl p-toluenesulphonate (1.9 g.) was heated on the steam-bath for 10 minutes and then treated with a solution of 2-3'-phenylphenoxypropylamine (2.3 g.) in ethanol (5 ml.). The mixture was swirled until homogeneous, allowed to stand at room temperature for 24 hours and then treated with an excess of a saturated aqueous solution of sodium p-chlorobenzenesulphonate. The precipitated solid was filtered and dried in vacuo. Recrystallisation from a mixture of ethanol and ether and then from a mixture of acetone and water gave N-(2-3'-phenylphenoxypropyl)-3,4-dimethylphenylacetamidine-p-chlorobenzenesulphonate, m.p. 86°–91°.

The 3,4-dimethylphenyl(thioacetamide) was prepared by passing a slow stream of hydrogen sulphide through a solution of 3,4-dimethylphenylacetonitrile (56.6 g.) in pyridine (60 ml.) and triethylamine (39.4 g.) during 12 hours. The reaction mixture was evaporated under reduced pressure and the residue was recrystallised from a mixture of benzene and light petroleum (b.p. 60°–80°) to give 3,4-dimethylphenyl (thioacetamide), m.p. 91°–94°.

EXAMPLE 94

The reaction between 3-methylphenyl(thioacetamide) (1.3 g.), methyl-p-toluenesulphonate (1.4 g.) and 2-3'-phenylphenoxypropylamine (1.8 g.) was carried out exactly; by the method of the relevant part of Example III. The product was crystallised first from a mixture of ethanol and ether and then from a mixture of acetone and water to give N-(2-3'-phenylphenoxypropyl)-3-methylphenylacetamidine-p-chlorobenzonesulphonate, m.p. 61°–65°.

The intermediate 3-methylphenyl(thioacetamide), m.p. 68°–72°, was prepared from 3-methylphenylacetonitrile by the method of the last part of Example III.

EXAMPLE 95

Freshly distilled 2-aminopropanol (9.9 g.) was stirred and heated gently during the portionwise addition of sodium (2.5 g.). Stirring and heating were continued until all the sodium had reacted and toluene (20 ml.) was added. The mixture was then heated to gentle reflux and treated dropwise, over 1 hour, with 3-benzyloxybenzyl chloride (15.3 g.). Heating was continued for a further 4 hours and the mixture cooled and filtered, and the precipitate was washed with toluene. The combined filtrate and washings were washed four times with water, dried over anhydrous potassium carbonate and evaporated. The residue was distilled under reduced pressure to give 2-3'-benzyloxybenzyloxypropylamine, b.p. 150°–155°/0.5 mm.

The reaction between this amine (2.7 g.) and 4-chlorophenylacetamidine hydrochloride (2.1 g.) was carried out as described in the last part of Example I. The reaction mixture was treated with slight excess of an aqueous solution of sodium p-toluenesulphonate. The resulting crystalline precipitate was filtered and recrystallised from a mixture of ethanol and water and from a mixture of ethanol and ether containing a few drops of water to give N-(2-3'-benzyloxybenzyloxypropyl)-4-chlorophenylacetamidine-p-toluene-sulphonate monohydrate, m.p. 92°–95°, after drying at ambient temperature and pressure.

EXAMPLE 96

By the methods of the relevant parts of Example I, 4-benzyloxyphenol was converted to 2-4'-benzyloxyphenoxypropionitrile, b.p. 166°–172°/0.7 mm., m.p. 84-86° (95% ethanol) and thence to 2-4'-benzyloxyphenoxypropylamine, b.p. 158-160°/0.12 mm.

The reaction between the amine (2.6 g.), 3,4-dimethylphenyl(thioacetamide) (1.8 g.) and methyl p-toluenesulphonate (1.9 g.) was carried out by the method of the second paragraph of Example III. The reaction mixture was treated with an excess of an aqueous solution of sodium naphthalene-2-sulphonate. The crystalline product was recrystallised from a mixture of ethanol and water and from a mixture of ethanol and ether to give N-(2-4'-benzyloxyphenoxypropyl)-3,4-dimethylphenylacetamidine naphthalene-2-sulphonate, m.p. 82°–86°.

EXAMPLE 97

A solution of sodium cyanide (5.9 g.) in dimethyl sulphoxide (40 ml.) was treated with 3-benzyloxybenzyl chloride (23.2 g.) and the reaction mixture stirred and maintained at 60° for 1 hour. The mixture was poured into water and the product was isolated with ether in the usual manner to give 3-benzyloxyphenylacetonitrile, b.p. 162°–166°/0.55 mm.

A solution of this nitrile (10.9 g.) in dry chloroform (30 ml.) and dry ethanol (2.4 g.) was saturated with gaseous hydrogen chloride, allowed to stand for two days, and then treated with a slight excess of saturated ethanolic ammonia. After a further two days the mixture was filtered and the filtrate evaporated to small bulk and treated with an excess of 2N-aqueous sodium p-toluenesulphonate. The resulting product was recrystallised from ethanol containing a few drops of water to give 3-benzyloxyphenylacetamidine p-toluenesulphonate, m.p. 189°–190°.

A mixture of this amidine salt (3.1 g.) and 2-3'-methoxyphenoxypropylamine (1.4 g.) in alcohol (15 ml.) was heated to reflux for 4 hours and then cooled slightly and diluted with ether. The resulting crystalline product was recrystallised from a mixture of ethanol and ether to give N-(2-3'-methoxyphenoxypropyl)-3-benzyloxyphenylacetamidine p-toluenesulphonate, m.p. 116°–118°.

EXAMPLE 98

3-Phenoxyphenol was converted by the methods of Example I to 2-3'-phenoxyphenoxypropionitrile, b.p. 127-130°/0.1 mm., thence to 2-3'-phenoxyphenoxypropylamine, b.p. 207-210°/13 mm. The reaction between this amine (1.8 g.), 3-methylphenyl (thioacetamide) (1.2 g.) and methyl p-toluenesulphonate (1.45 g.) did not yield a crystalline salt, and the total reaction mixture, containing N-L 2-3'-phenoxyphenoxypropyl)-3-methylphenylacetamidine -p-toluenesulphonate, was used for biological testing.

EXAMPLE 99

Tablets (0.555 g.) were made by mixing N-(2-2'-benzyloxyphenoxypropyl)-4-chlorophenylacetamidine p-toluene sulphate (0.25 g.), in a fine powder with lactose (0.25 g.) and starch (0.05 g.), granulating the mixture with alcohol, alcholic polyvinyl pyrrolidone or a mixture of equal parts of alcohol and water, drying the granules at 40°, adding magnesium stearate (0.005 g.) as a lubricant, and compressing the mixture directly.

EXAMPLE 100

Tablets (0.505 g.) were made by granulating N-(2-2'-benzyloxyphenoxypropyl)-4-chlorophenylacetamidine p-toluenesulphonate (0.5 g.) in a fine powder with equal parts of alcohol and water, adding magnesium stearate (0.005 g.) as a lubricant, and compressing the mixture directly.

EXAMPLE 101

The reaction between 3,4-dimethylphenyl(thioacetamide( (1.8 g.), methyl p-toluenesulphonate (1.9 g.) and 2-3'-phenoxyphenoxypropylamine (2.4 g.) was carried out by the method of the second paragraph of Example 93. The product could not be crystallised. Therefore the total reaction mixture was converted, with aqueous hydroxide, to the base; this was treated with one equivalent of aqueous hydrochloric acid to give a solution of crude N-(2-3'-phenoxyphenoxypropyl)-3,4-dimethylphenylacetamidine hydrochloride which was used directly for biological testing.

EXAMPLE 102

By the methods of the relevant parts of Example 91, 3-benzylphenol was converted to 2-3'-benzylphenoxypropionitrile, b.p. 140°–146°/0.2 mm and thence to 2-3'-benzylpropylamine, b.p. 152°–154°/0.5 mm. The reaction between 3,4-dimethylphenyl(thioacetamide) (1.8 g.), methyl p-toluenesulphonate (1.9 g.) and 2-3'-benzylphenoxypropionitrile (2.4 g.) was carried out by the method of the second paragraph of Example 93. The product was isolated as the 2-naphthalenesulphonate as in Example 96. The resulting N-(2-3'-benzylphenoxypropyl)-3,4-dimethylphenylacetamidine 2-naphthalenesulphonate had m.p. 103°–105° after recrystallisation from a mixture of ethanol and ether, and from ethyl acetate.

EXAMPLE 103

Table 3 (contd.).

Hydrochlorides of Amidines, R.NH.C(=NH).CH$_2$.Ar

| Example | R | Amine R.NH$_2$ method | Ar | m.p. | Crystallisation solvent* |
|---|---|---|---|---|---|
| 103 | 2-(5-chloro-2-thenyloxy)ethyl | D | 3-methylphenyl | 70–73° monohydrate | 2 |

*See footnotes to Table 1.

EXAMPLES 104–106

Table 4 (contd.).

p-Toluenesulphonate Salts of Amidines R.NH.C(=NH).CH$_2$.Ar

| Example | R | Amine R.NH$_2$ method | Ar | m.p. | Crystallisation solvent* |
|---|---|---|---|---|---|
| 104 | 2-(5-chloro-2-thenyloxy)propyl | D | 3,4-dimethylphenyl- | 141–143° | 1 and 7 |
| 105 | 2-3'-chlorobenzyl-oxypropyl | D | 3-methylphenyl | 55–58° monohydrate | 3 |
| 106 | 2-(5-chloro-2-thenyloxy)propyl | D | 3-methylphenyl | 127–129° | 1 and 7 |

*See footnotes to Table 1.

EXAMPLE 107

Table 6 (contd.).

p-Toluenesulphonate Salts of Amidines R.NH.C(=NH).CH$_2$.Ar

| Example | R | Amine R.NH$_2$ method | Ar | m.p. | Crystallisation solvent* |
|---|---|---|---|---|---|
| 107 | 2-3'chlorobenzyl-oxypropyl | D | 3,4-dimethyl-phenyl | 129–131° | 7 and 1 |

*See footnotes to Table 1

EXAMPLE 108

The product was prepared by the method of Example 83. It was recrystallised from a mixture of ethanol and ether and from a mixture of acetone and ether to give pure N-(2-3'-methoxyphenoxypropyl)-3,4-dichlorophenylacetamidine hydriodide, m.p. 153°–154°. The intermediate 3,4-dichlorophenyl(thioacetamide) had m.p. 119°–120° after recrystallisation from ethanol, and methyl 3,4-dichlorophenyl(thioacetimidate) hydriodide had m.p. 143°–145°.

EXAMPLES 109–117

The amidine p-toluenesulphonates of Table 10 were prepared by the method of Example 84. This consisted of the reaction between methyl p-toluenesulphonate and an aryl(thioacetamide) Ar.CH$_2$.CS.NH$_2$ to give the intermediate S-methyl aryl(thioacetimidate) p-toluenesulphonate, which was then treated with a primary amine R.NH$_2$. The preparation of 3-methylphenyl(thioacetamide) is described in Example 83; by the same method, starting from 3,4-dimethylphenyl acetonitrile, was prepared 3,4-dimethylphenyl(thioacetamide), m.p. 91°–94°, after recrystallisation from a mixture of benzene and light petroleum (b.p. 40°–60°).

Table 10 p-Toluenesulphonate Salts of Amidines R.NH.C(=NH).CH$_2$.Ar

| Example | R | Amine R.NH$_2$ method | Ar | m.p. | Crystallisation solvent* |
|---|---|---|---|---|---|
| 109 | 2-3'-fluorophenoxypropyl | B | 3,4-dimethylphenyl | 113–116° | 4 and 1 |
| 110 | 2-3'-chlorophenoxypropyl | B | 3,4-dimethylphenyl | 115–118° | 4 and 1 |
| 111 | 2-3'-fluorophenoxypropyl | B | 3-methylphenyl | 117–119° | 4 and 1 |
| 112 | 2-2'-chlorobenzyl-oxypropyl | D | 3,4-dimethylphenyl | 85–89° monohydrate | 2 and 4 |
| 113 | 2-2'-chlorobenzyl-oxypropyl | D | 3-methylphenyl | 74–76° monohydrate | 2 |
| 114 | 2-3'-bromophenoxypropyl | B | 3-methylphenyl | 121–124° | 4 and 1 |

Table 10 -continued p-Toluenesulphonate Salts of Amidines R . NH . C(=NH) . CH$_2$ . Ar

| Example | R | Amine R.NH$_2$ method | Ar | m.p. | Crystall- isation solvent* |
|---|---|---|---|---|---|
| 115 | 2-3'-bromophenoxy- propyl | B | 3,4-dimethyl- phenyl | 77–79° monohydrate | 4 and 3 |
| 116 | 2-3'-(methylthio)- phenoxy propyl | B | 3,4-dimethyl- phenyl | 120–122° | 1 and 7 |
| 117 | 2-3'-(methylthio)- phenoxy propyl | B | 3-methylphenyl | 82–84° monohydrate | 1 and 7 |

*See footnotes to Table 1

EXAMPLES 118-121

The amidines, of Table 11, were prepared by previously described methods but to isolate the product the reaction mixture was treated with a slight excess of a saturated aqueous solution of sodium 2-naphthalenesulphonate to precipitate the amidine as its 2-naphthalenesulphonate salt. Example 118 was prepared by the reaction between the primary amine and S-methyl 3,4-dimethyl(thioacetamidate) hydriodide as described in Example 83. Examples 119–121 were prepared by the methods of Examples 109 to 117.

Table 11

2-Naphthalenesulphonate Salts of Amidines R . NH . C(=NH) . CH$_2$ . Ar

| Example | R | Amine R.NH$_2$, method | Ar | m.p. | Crystall- isation solvent* |
|---|---|---|---|---|---|
| 118 | 2-3'-t-butyl phenoxypropyl | B | 3,4-dimethyl- phenyl | 85–90° | 7 |
| 119 | 2-phenylthiopropyl | B | 3-methylphenyl | 129–131° | 1 |
| 120 | 2-3'-methoxyphenyl- thiopropyl | B | 3,4-dimethyl- phenyl | 99–102° | 2 and 4 |
| 121 | 2-2'-phenoxyethoxy- ethyl | — | 3,4-dimethyl- phenyl | 55–60° | 7 |

*See footnotes to Table 1

Table 8 (contd.).

Preparation of Intermediate Primary Amines

| Ar | Boiling Points | |
|---|---|---|
| | Ar.O.CHMe.CN | Ar.O.CHMe.CH$_2$NH$_2$ |
| 3-fluorophenyl | 120–123°/18 mm. | 111–113°/15 mm. |
| 3-bromophenyl | 150–156°/12 mm. | 151–156°/14 mm. |
| 3-(methylthio)phenyl | 176–180°/15 mm. | 176–179°/16 mm. |
| 3-t-butylphenyl | 140–144°/13 mm. | 96–100°/0.4 mm. |

2-Phenylthiopropylamine, b.p. 138°–144°/14 mm., and 2-3'-methoxyphenylthiopropylamine, b.p. 92°–96°/0.05 mm., were also prepared by the lithium hydride reduction of the corresponding nitriles, according to the second part of Method B. The hitherto undescribed 2-3'-methoxyphenylthiopropionitrile was prepared as follows:

3-Methoxy(thiopheol) (10 g.) was added to a solution of sodium (1.5 g.) in dry methanol (16 ml.). The solution was cooled to 0°, treated dropwise with 2-chloropropionitrile (9.0 g) and then stirred at room temperature for 1 hour. The solution was then diluted with ether and filtered. The filtrate was washed with water, dried over anhydrous sodium sulphate and evaporated. The residue was distilled to give pure 2-3'-methoxyphenylthiopropionitrile, b.p. 172°–176°/18 mm.

The following amines were prepared by Method D:
2-(5-chloro-2-thenyloxy)propylamine, b.p. 93°–96°/0.1 mm.
2-2'-chlorobenzyloxypropylamine, b.p. 148°–154°/16 mm.
2-3'-chlorobenzyloxypropylamine, b.p. 158°–162°/17 mm.
2-(5-chloro-2-thenyloxy)ethylamine, b.p. 88°–90°/0.1 mm.

What I claim is:

1. A pharmaceutical composition containing a pharmaceutically effective serotonin antagonizing amount of an amidine of the formula:

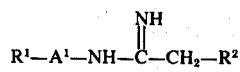

$$R^1-A^1-NH-\overset{NH}{\underset{\|}{C}}-CH_2-R^2$$

or a pharmaceutically acceptable acid addition salt thereof wherein R$^1$ or R$^2$ are phenyl or thien-2-yl optionally substituted in one, two, or three positions by substituents halogen, lower alkyl, lower alkoxy, hydroxy, lower alkylthio, phenyl, phenoxy, phenyl - (lower alkyl) or phenyl - (lower alkoxy), each of said substituents phenyl, phenoxy, phenyl - (lower alkyl) and phenyl-(lower alkoxy) being optionally substituted in one or two positions by a member selected from the class consisting of halogen, lower alkyl, lower alkoxy, hydroxy and lower alkylthio;

A$^1$ is a divalent straight or branched alkylene group containing from two to six carbon atoms and one or two divalent atoms which are each an oxygen or sulphur atom; provided that there are at least two carbon atoms between the divalent atom and the -NH - group and between the two divalent atoms, and a pharmaceutically acceptable carrier therefore.

2. A composition according to claim 1 in which R$^1$ is phenyl optionally substituted in one or two positions by phenyl, benzyl, phenoxy — (lower alkoxy), halogen, lower alkyl or lower alkoxy;

A¹ is an oxalkylene group - O.R³ - where R³ is divalent alkylene group containing 2 to 4 carbons, and R² is phenyl optionally substituted in one or two positions by halogen, lower alkyl or lower alkoxy.

3. A composition according to claim 1 in which R¹ is phenyl optionally substituted in the 3- position by chlorine, bromine, methoxy, ethoxy, methyl and ethyl;

A¹ is an oxyalkylene group — O.R.³— where R³ is butyl-2, 3-ene, isopropylene, ethylene, 2-propyl-1-ene and 1-propyl-2-ene; and R² is phenyl optionally substituted in the 3- position, the 4- position, the 3, 5- position, the 2, 4- positions and the 3, 4 positions by chlorine, methyl or methoxy.

4. A composition according to claim 1 in which R¹ is thien -2-yl, A¹ is methyleneoxyalkylene group — Ch₂ OR³ - where R³ is a divalent alkylene group containing 2 to 4 carbons and R² is phenyl optionally substituted in one or two positions by halogen, lower alkyl or lower alkoxy.

5. A composition according to claim 1, wherein said amidine is N-(2-3- methoxy phenoxypropyl) —3-methylphenylacetamidine and pharmaceutically acceptable salt thereof.

6. A composition according to claim 1 wherein said amidine is N-(2-m-benzylphenoxypropyl) -3, 4-dimethylphenylacetamidine and pharmaceutically acceptable salt thereof.

7. A composition according to claim 1 wherein said amidine is N - (2-m-phenoxyphenoxypropyl) -3, 4- dimethylphenylacetamidine and pharmaceutically acceptable salt thereof.

8. A composition according to claim 1 wherein said amidine is N-[2-m-(methylthio)phenoxypropyl] - 3, 4- dimethylphenylacetamidine and pharmaceutically acceptable salt thereof.

9. A composition according to claim 1 wherein said amidine is N-[2-(5-chloro-2-thenyloxy)propyl]-3, 4-dimethylphenylacetamidine and pharmaceutically acceptable salt thereof.

10. A composition according to claim 1 wherein said amidine is N-(2-m-methylthiophenoxypropyl)-m-methylphenylacetamidine and pharmaceutically acceptable salt thereof.

11. A composition according to claim 1 wherein said amidine is N-(2-2¹-thenyloxypropyl)-3, 4- dimethylphenylacetamidine and pharmaceutically acceptable salt thereof.

12. A composition according to claim 1 wherein said amidine is N-(2-m-fluorophenoxypropyl)-m-methylphenylacetamidine and pharmaceutically acceptable salt thereof.

13. A composition according to claim 1 wherein said amidine is N-(2-fluorophenoxypropyl)-3, 4-dimethylphenylacetamidine and pharmaceutically acceptable salt thereof.

14. A pharmaceutical composition according to claim 1 comprising in combination an amidine of the formula

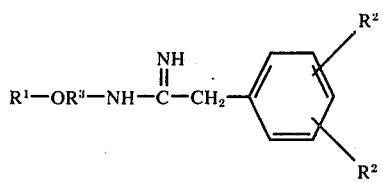

or a pharmaceutically acceptable acid addition salt thereof wherein R³ is divalent alkylene having 2 to 4 carbons, R² is hydrogen, lower alkyl, lower alkoxy, halogen or benzyloxy and R¹ is

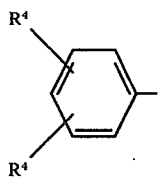

wherein R⁴ is lower alkyl, lower alkoxy, halogen, hydrogen, benzyloxy, phenoxy, lower alkylthio, benzyl or phenyl and a pharmaceutically acceptable carrier therefor.

15. A pharmaceutical composition according to claim 1 comprising a compound of the formula

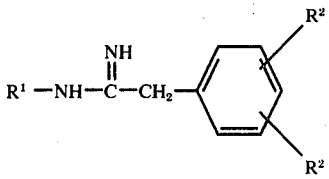

or a pharmaceutically acceptable acid addition salt thereof wherein R¹ is 2-2¹ thenyloxypropyl or 2-(5-chloro-2-thenyloxy) propyl and wherein R² is hydrogen, halogen or lower alkyl and a pharmaceutically acceptable carrier therefor.

16. A pharmaceutical composition according to claim 1 comprising a compound selected from the class consisting of N-(2-3¹-methylbenzyloxypropyl9-4-chlorophenylacetamidine, N-(2-3¹-benzyloxybenzyloxypropyl)-4-chlorophenylacetamidine, N-(2-m-chlorobenzyloxypropyl)-3,4-dimethylphenylacethamidine and pharmaceutically acceptable acid addition salt thereof and a pharmaceutically acceptable carrier therefor.

17. A pharmaceutical composition according to claim 1 comprising N-(2-phenylthiopropyl)-m-methylphenylacetamidine or a pharmaceutically acceptable salt thereof and a pharmaceutically carrier therefor.

18. A method of antagonizing 5-hydroxytryptamine or its formation in the body of an animal which comprises administering to an animal an effective serotonin antagonizing amount of

or a pharmaceutically acceptable acid addition salt thereof wherein R¹ and R² are phenyl or thien-2-yl optionally substituted in one, two, or three positions by substituents halogen, lower alkyl, lower alkoxy, hydroxy, lower alkylthio, phenyl, phenoxy, phenyl - (lower alkyl) or phenyl - (lower alkoxy, each of said substituents phenyl, phenoxy, phenyl-(lower alkyl) and phenyl-(lower alkoxy) being optionally substituted in one or two positions by a member selected from the class consisting of halogen, lower alkyl, lower alkoxy, hydroxy and lower alkylthio;

$A^1$ is a divalent straight or branched alkylene group containing from two to six carbon atoms and one or two divalent atoms which are each an oxygen or sulphur atom, provided that there are at least two carbon atoms between the divalent atom and the — NH — group and between the two divalent atoms, and a pharmaceutically acceptable carrier therefor.

19. A method according to claim 18 in which $R^1$ is phenyl optionally substituted in one or two positions by phenyl, benzyl, phenoxy - (lower alkoxy), halogen, lower alkyl or lower alkoxy;

$A^1$ is an oxalkylene group — $O.R^3$ — wherein $R^3$ is divalent alkylene group containing 2 to 4 carbons, and $R^2$ is phenyl optionally substituted in one or two positions by halogen, lower alkyl or lower alkoxy.

20. A method according to claim 18 in which $R^1$ is phenyl optionally substituted in the 3- position by chlorine, bromine, methoxy, ethoxy, methyl and ethyl, $A^1$ is an oxyalkylene group — $O.R^3$ — wherein $R^3$ is butyl-2, 3-ene, isopropylene, ethylene, 2-propyl-1-ene and 1-propyl-2-ene; and $R^2$ is phenyl optionally substituted in the 3- position, the 4- position, the 3, 5- position, the 2, 4- positions and the 3, 4 positions by chlorine, methyl or methoxy.

21. A method according to claim 18 in which $R^1$ is thien -2-yl, $A^1$ is methyleneoxyalkylene group — $CH_2OR^3$- wherein $R^3$ is a divalent alkylene group containing 2 to 4 carbons and $R^2$ is phenyl optionally substituted in one or two positions by halogen, lower alkyl or lower alkoxy.

22. A method according to claim 18 in which said amidine is N-(2-3- methoxy phenoxypropyl) -3- methylphenylacetamidine and pharmaceutically acceptable salt thereof.

23. A method according to claim 18 wherein said amidine is N-(2-m-benzylphenoxypropyl)-3, 4- dimethylphenylacetamidine and pharmaceutically acceptable salt thereof.

24. A method according to claim 18 wherein said amidine is N-(2-m-phenoxyphenoxypropyl)-3, 4- dimethylphenylacetamidine and pharmaceutically acceptable salt thereof.

25. A method according to claim 18 wherein said amidine is N-[2-m-(methylthio) phenoxypropyl] - 3, 4- dimethylphenylacetamidine and pharmaceutically acceptable salt thereof.

26. A method according to claim 18 wherein said amidine is N-[2-(5-chloro-2-thenyloxy)propyl]-3, 4- dimethylphenylacetamidine and pharmaceutically acceptable salt thereof.

27. A method according to claim 18 wherein said amidine is N-(2-m-methylthiophenoxypropyl)-m-methylphenylacetamidine and pharmaceutically acceptable salts thereof.

28. A method according to claim 18 wherein said amidine is N-(2-2¹-thenyloxypropyl)-3,4-dimethylphenylacetamidine and pharmaceutically acceptable salt thereof.

29. A method according to claim 18 wherein said amidine is N-(2-m-fluorophenoxypropyl)-m-methylphenylacetamidine and pharmaceutically acceptable salt thereof.

30. A method according to claim 18 wherein said amidine is N-(2-m-fluorophenoxypropyl)-3, 4-dimethylphenylacetamidine and pharmaceutically acceptable salt thereof.

31. A method according to claim 18 comprising in combination an amidine of the formula

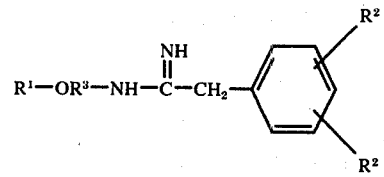

or a pharmaceutically acceptable salt acid addition salt thereof wherein $R^3$ is divalent alkylene having 2 to 4 carbons, $R^2$ is hydrogen, lower alkyl, lower alkoxy, halogen or benzyloxy and $R^1$ is

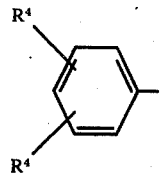

wherein $R^4$ is lower alkyl, lower alkoxy, halogen, hydrogen, benzyloxy, phenoxy, lower alkylthio, benzyl, or phenyl and a pharmaceutically acceptable carrier therefor.

32. A method according to claim 18 comprising a compound of the formula

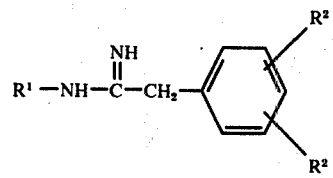

or a pharmaceutically acceptable acid addition salt thereof wherein $R^1$ is 2-2¹-thenyloxypropyl or 2-(5-chloro-2-thenyloxy) propyl and wherein $R^2$ is hydrogen, halogen or lower alkyl and a pharmaceutically acceptable carrier therefor.

33. A method according to claim 18 comprising a compound selected from the class consisting of N-(2-3¹-methylbenzyloxypropyl)-4-chlorophenylacetamidine, N-(2-3¹-benzyloxybenzyloxypropyl)-4-chlorophenylacetamidine, N-(2-m-chlorobenzyloxypropyl)-3,4-dimethylphenylacetamidine and pharmaceutically acceptable acid addition salt thereof and a pharmaceutically acceptable carrier therefor.

34. A method according to claim 18 comprising N-(2-phenylthiopropyl)-m-methylphenylacetamidine or a pharmaceutically acceptable salt thereof and a pharmaceutically acceptable carrier therefor.

35. A method according to claim 18 in which the animal is a rat and is administered 5-hydroxytryptamine and then is administered an effective 5-hydroxytryptamine antagonizing amount of the composition to study the effect of 5-hydroxytryptamine in a rat.

* * * * *